United States Patent [19]

Cronenberg

[11] 4,327,718

[45] May 4, 1982

[54] CONTINUOUSLY DRAINING TRAP FOR REMOVAL OF CONDENSATE FROM A PATIENT BREATHING CIRCUIT

[75] Inventor: Richard A. Cronenberg, Ramsey, N.J.

[73] Assignee: Becton, Dickinson and Company, Paramus, N.J.

[21] Appl. No.: 188,393

[22] Filed: Sep. 18, 1980

[51] Int. Cl.³ .............................................. A61M 16/00
[52] U.S. Cl. .......................... 128/205.12; 128/205.27; 55/461; 55/466; 55/DIG. 35
[58] Field of Search ...................... 128/200.14, 200.16, 128/203.12, 203.16, 203.25, 203.28, 203.29, 204.13, 204.15, 204.16, 204.18, 204.21, 204.22, 204.23, 204.24, 204.25, 204.26, 205.11, 205.12, 205.18, 205.24, 205.25, 206.22, 205.27; 55/524, 466, DIG. 35, 461

[56] References Cited

U.S. PATENT DOCUMENTS

| 3,454,005 | 7/1969 | Eubanks et al. | 128/203.12 |
| 3,631,654 | 1/1972 | Riely et al. | 55/524 |
| 4,020,834 | 5/1977 | Bird | 128/204.25 |
| 4,171,209 | 10/1979 | Brown | 55/466 |

*Primary Examiner*—Henry J. Recla

[57] ABSTRACT

A drain device for the continuous removal of condensate from an operational patient breathing circuit comprises a body having a first opening adapted for connection to a patient breathing apparatus. A second opening in the body is adapted for connection to a patient breathing device. There is a passageway in the body which provides fluid communication between these openings, with a third opening through the body communicating with the passageway. A liquid-pervious, gas-impervious material covers the third opening so that condensate can continuously drain through the third opening while the breathing circuit is in operation.

5 Claims, 4 Drawing Figures

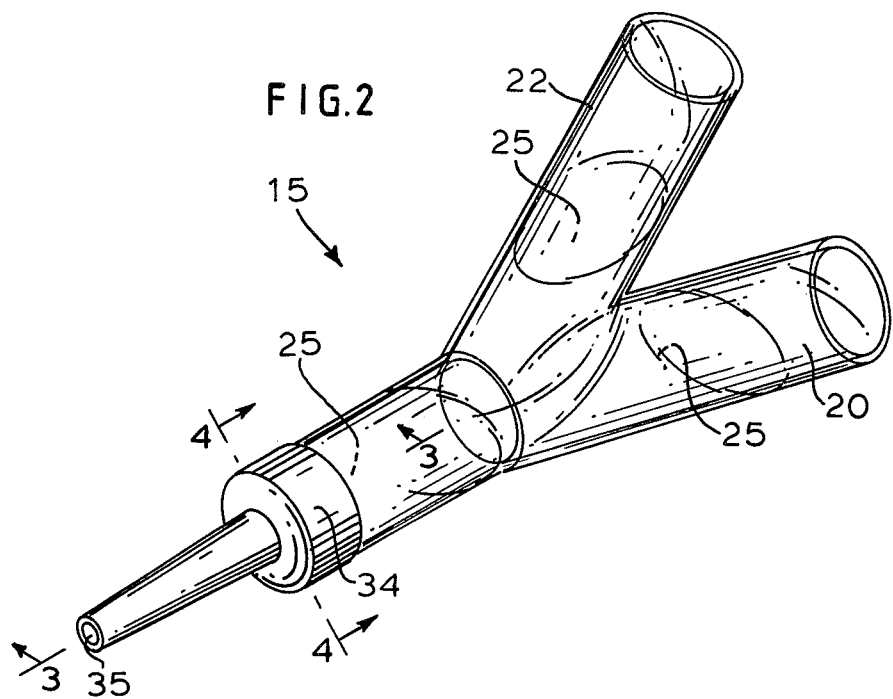
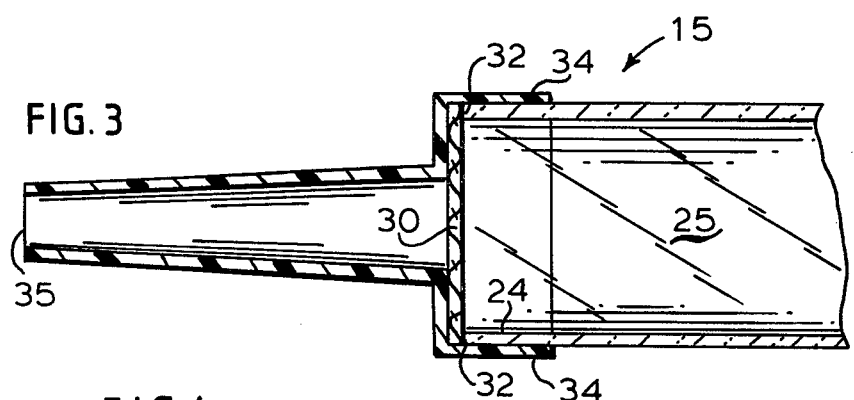
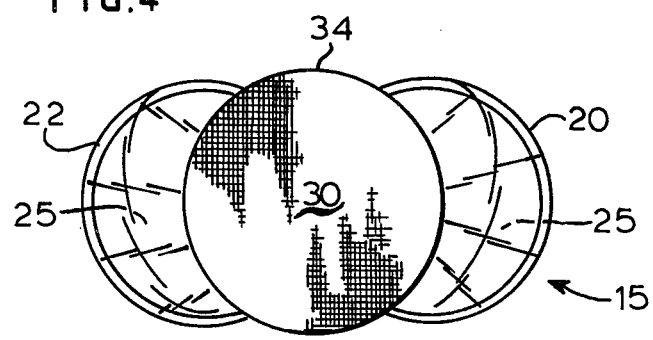

CONTINUOUSLY DRAINING TRAP FOR REMOVAL OF CONDENSATE FROM A PATIENT BREATHING CIRCUIT

BACKGROUND OF THE INVENTION

1. Field of the Invention

The present invention relates to a drain device for removal of condensate from an operational patient breathing circuit, and more particularly, concerns a continuously draining trap which allows condensate, but not gas, to drain from the patient breathing circuit while under pressure.

2. Description of the Prior Art

In respiratory therapy and anesthesia devices employed in patient breathing circuits for a variety of circumstances and reasons, various gases, air or vapors are delivered to the patient. For instance, mechanical ventilators are used to augment respiratory gas flow in circumstances where the patient may be experiencing respiratory failure. In these apparatuses, the breathing frequency and inspiratory and expiratory phases of ventilation can be varied by controlling the apparatus to meet the individual needs of the patient. Different ventilators may be employed also depending upon the condition of the patient: assisted ventilation is used in patients who have spontaneous respiration but who may have inadequate alveolar ventilation, whereas controlled ventilation is used in those patients with few or no spontaneous respirations. These ventilators will inflate the patient's lungs with air under pressure from the ventilator until either a preset pressure or preset volume, depending upon choice of apparatus, is achieved. When this preset level is reached, inspiration ends and expiration begins.

Similar devices are used on patients with chest diseases who receive Intermittent Positive Pressure Breathing (IPPB) treatments. An IPPB treatment may include the delivery of vapors to the patient in conjunction with a nebulizer in the patient breathing circuit. Delivery of the vapors is made to the patient by virtue of a closed breathing circuit, oftentimes under pressure, to assure proper delivery. In inhalation anesthesia circuits, the gas mixtures are also delivered to the patient under pressure in accordance with the proper control mechanisms.

One of the problems which occur in both pressurized and un-pressurized gas or vapor delivery systems involves the undesirable collection of condensate generally in the tubing which extends from the control apparatus to the patient. This condensate occurs since these gases or vapors in the line contain a certain amount of humidity before entering the patient. Once condensation starts to build up in the line, it must be removed to improve patient comfort and also to prevent the patient from inspiring too much water. Water traps in these patient breathing circuit lines have been in existence for some time, but are deficient in many respects. For instance, the known water traps tend to collect water within and must be drained about every hour. Some of these water traps are very large and increase the compressible volume of the patient circuit. When filled with water, they add a considerable amount of strain to the circuit caused by the weight of the accumulated water. Some of the smaller volume water traps tend to lose effectiveness by dumping water back into the patient circuit if the patient should move or pull the tubing. These smaller volume traps also must be drained more frequently. When draining occurs in both small and large existing water traps, the patient circuit, if operating under pressure, must be shut down and depressurized when the water is being emptied from the trap. Of course, during the depressurized condition, delivery of the gas, air or vapors to the patient is interrupted.

It can be seen that manual draining of the existing traps is time consuming and requires periodic monitoring by the attendants to observe when the trap is becoming filled. In addition, the interruption of the service to the patient during depressurization of a pressurized patient breathing circuit is undesirable. With these major problems in mind, there has been a need in this field of patient breathing circuits to provide a water trap or draining device which will simplify the tasks of the respiratory therapist while at the same time improving inhalation service to the patient. It is to this end that the present invention is directed.

SUMMARY OF THE INVENTION

A drain device for the continuous removal of condensate from an operational patient breathing circuit comprises body means having a first opening adapted for connection to a patient breathing apparatus. A second opening is adapted for connection to patient breathing means with a passageway within the body means providing fluid communication between the first and second openings. A third opening through the body means communicates with the passageway. A liquid-pervious, gas-impervious material covers the third opening so that condensate can continuously and automatically drain through the third opening while the breathing circuit is in operation.

In the preferred embodiment of this aspect of the invention, the drain device is a trap comprised of a hollow, plastic Y-shaped tubular member. The drain opening is at the end of the base of this Y-shaped member. By attaching the commonly used flexible tubing to the respective arms of the water trap, it may be positioned in the patient's breathing circuit so that water can continuously drain out the base of the trap under force of gravity. Design of the liquid-pervious, gas-impervious material will allow liquid to drain therethrough, but not gas, up to operating pressures inside the tubing of about five pounds per square inch (approximately 350 grams per square centimeter).

Another aspect of the present invention includes a patient breathing apparatus. This apparatus comprises means for controllably providing fluid from a source to a patient in accordance with a pre-established breathing rhythm or pattern. The apparatus further includes means for delivering the fluid to the patient. Means is associated with the delivery means for allowing condensate, but not gas, in the delivery means to continuously and automatically drain therefrom while the fluid is being delivered to the patient. The continuous draining means of this aspect of the invention is preferably the continuously draining water trap substantially as described above. This type of apparatus may also be pressurized in a closed system, with the fluid to be delivered to the patient under pressure.

From the structural standpoint, there is believed to be no water trap, or similar draining device, disclosed for or used with patient breathing circuits which allows the continuous, uninterrupted draining of condensate from the tubing circuitry to the patient. Inasmuch as the present invention provides for the continuous, uninterrupted draining of condensate from the line, it satisfies this longfelt demand for this type of improvement in patient breathing circuits. As a continuous draining device, the present invention eliminates the need for manual draining as is required in presently employed water traps. Considerable time is therefore saved since the patient therapist does not have to perform this manual draining task when using the water trap of the present invention. The ability of the present water trap to operate while the patient breathing circuit is pressurized is a considerable advantage over the prior water traps since there will be no need to interrupt the service to the patient. Furthermore, the present water trap can be made small and lightweight so that it may be efficiently employed in standard and customary tubing lines between the breathing apparatus and the patient. In this configuration, no supplementary equipment is required to drain water from the trap of the present invention, inasmuch as it can be oriented in the tubing circuitry so that condensate, but not gas, drains automatically by force of gravity.

BRIEF DESCRIPTION OF THE DRAWINGS

FIG. 2 is an enlarged perspective view of the preferred continuously draining trap as shown in FIG. 1;

FIG. 3 is a cross-sectional view taken along line 3—3 of FIG. 2; and

FIG. 4 is a cross-sectional view taken along line 4—4 of FIG. 2.

DETAILED DESCRIPTION

Figure 1:
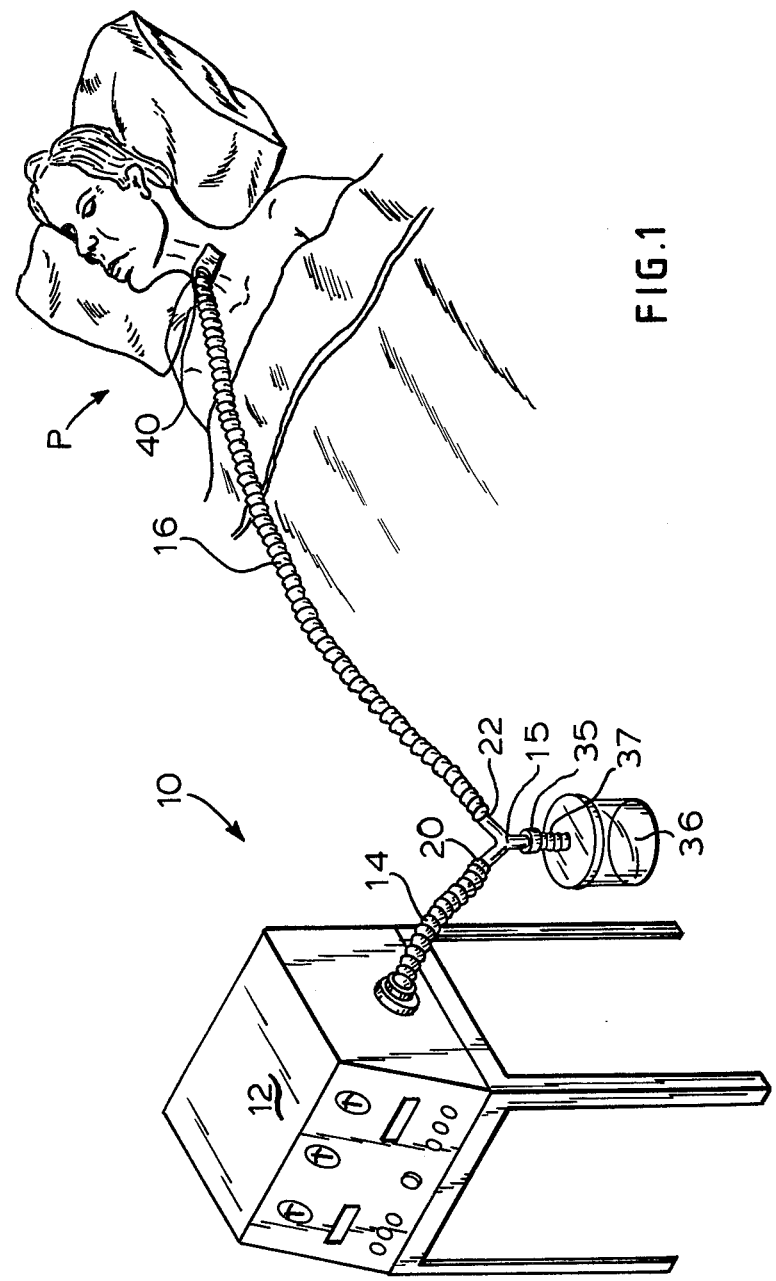
FIG. 1 is a perspective view illustrating one embodiment of a patient breathing circuit during use which includes the preferred embodiment of the continuously draining trap of the present invention.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Turning now to the drawings, and FIG. 1 in particular, there is illustrated a patient breathing apparatus 10 as it may appear during use with a patient P. Apparatus 10 consists generally of three components: a controllable patient breathing device 12, a length of flexible tubing 14 extending from the breathing device to a continuously draining water trap 15 and another section of flexible tubing 16 extending to patient P.

Patient breathing device 12 may be any of the well known devices for delivering gases, vapors, air or the like to a patient in applications such as ventilation, inhalation, anesthesia and respiratory therapy. For instance, patient breathing device 12 may be a mechanical ventilator, either of the pressure-preset or the volume-preset types. In controllably delivering fluid, e.g., under pressure to the patient, this breathing device either includes a source of fluid within or is connected to such a source so that it may be passed on to the patient. In addition, a typical ventilator allows the breathing frequency and inspiratory and expiratory phases of ventilation to be varied to meet the individual needs of the patient, with a variety of settings available to the attendant in establishing the correct breathing rhythm each time the ventilator is used.

Flexible tubes 14 and 16 form part of the patient breathing circuit and are widely used in these kinds of patient breathing apparatuses. In most instances, these flexible tubes are of the corrugated variety since this configuration, in addition to being lightweight and flexible, has been most efficient in the delivery of gases and the like to the patient. When used in a pressurized patient breathing circuit such as the preferable one being described, flexible tubes 14 and 16 should be substantially non-porous so that the integrity of the pressurization may be maintained, while the correct amounts of gas can be controllably delivered to the patient.

As seen in FIGS. 2-4, taken in conjunction with FIG. 1, continuously draining water trap 15 is provided in the line between breathing device 12 and patient P. In order to best utilize this type of continuously draining trap, it is preferably shaped in a Y configuration, and is tubular in form so that the gases from the patient breathing device may pass through the trap on the way to the patient. At the end of one arm of the Y-shaped trap a fluid inlet opening 20 is formed. In use, flexible tube 14 is connected to fluid inlet opening 20 thereby establishing fluid communication to the patient breathing device. At the end of the other arm of the Y-shaped trap, a fluid outlet opening 22 is formed. Flexible tube 16 is connected to fluid outlet opening 22 so that fluid communication is now provided to the patient. At the base of the Y-shaped trap a third opening is provided serving as a drain opening 24. Trap 15 is completely hollow with a passageway 25 within interconnecting fluid inlet opening 20, fluid outlet opening 22 and drain opening 24. FIGS. 3 and 4 illustrate the details of the drain opening more clearly.

A liquid-pervious, gas-impervious membrane 30 is positioned in passageway 25 across the base of the Y-shaped trap. This membrane is positioned across passageway 25 so that it is close to and covers drain opening 24 at the end of the base. Preferably, membrane 30 is sealed to the base end 32 of the Y-shaped trap so as to cover drain opening 24. Depending on choice of materials for membrane 30, it is most desirable to heat seal the membrane to the base of the Y-shaped trap. This type of assembly contributes to providing a more effective seal across the passageway so that the integrity of pressurization in the system, if any, can be maintained. In the embodiment being described, a removable cap 34 is positioned over drain opening 24 and membrane 30 with a hollow nozzle 35 extending therefrom. Nozzle 35 directs the flow of condensate into the collection container 36 (as seen in FIG. 1). This capping of the base end of the trap also contributes to maintaining membrane 30 in a secured position.

Liquid-pervious, gas-impervious membrane 30 is preferably a liquid-wettable, hydrophilic, porous membrane. Once sufficiently wetted, this hydrophilic membrane will permit liquid, such as water, to pass therethrough but prevent gas from passing. In its preferred embodiment, membrane 30 is made of cellulose, although other materials may be chosen, and generally has a thickness of about 0.01 inches (0.025 centimeters). This membrane has a general pore size or rating of approximately 1.5 microns, although the pore size may be varied to suit the particular circumstances in which the continuously draining trap is being used. However, it may be desirable to select the pore size of the porous membrane so that bacteria can pass therethrough so that such bacteria will be shunted away from the patient. In this regard, the general pore size of the membrane would be greater than 0.22 microns, the pore size generally considered small enough to satisfactorily filter out bacteria. The net effect of these aforementioned parameters of membrane 30 will allow liquid, but not gas, to drain through the membrane even while the circuit is pressurized up to pressures of about five pounds per square inch (approximately 350 grams per square centimeter). In typical patient breathing circuits such as pressure-type mechanical ventilators, fluid in the flexible tubes would be delivered to the patient under a pressure up to about two pounds per square inch (140 grams per square centimeter). Accordingly, this type of liquid-pervious, gas-impervious membrane would provide a safety factor of about two and one-half (2½) which would be a comfortable level to assure that pressurization of the entire breathing circuit will not be compromised by having this continuously draining trap in the line.

It will be appreciated to those skilled in the art that variations of the parameters of the liquid-pervious, gas-impervious membrane can be devised which will afford working embodiments which will satisfy the aims of the present invention. Other than membrane 30, the remaining portions of the continuously draining trap are preferably made of rigid plastic in an inexpensive configuration to allow disposability.

In FIG. 1, continuously draining trap 15 can be seen during operation of a patient breathing circuit which may be pressurized. Gas, vapor or the like, from a source either in patient breathing device 12 or connected thereto, is delivered through flexible tubes 14 and 16 to patient P. The fluid passes through continuously draining trap 15 along the way. Fluid remains under pressure through the tubing and is ultimately delivered to the patient through a tracheostomy tube 40 connected to the patient. Inasmuch as the pressurized fluid generally contains some humidity for patient comfort, after some time there usually is a build up of condensate in tubes 14 and 16. Trap 15 is positioned so that nozzle 35 is pointing downwardly into a collection container 36. A flexible hose 37 facilitates the connection of nozzle 35 to container 36. In this orientation, the drain opening lies intermediate in the flow path between fluid inlet opening 20 and fluid outlet opening 22 in the trap. Preferably, the drain opening with nozzle 35 covering same is placed on the floor next to the patient, or some low lying region, so that nozzle 35 is at the lowermost position in the entire patient breathing circuit. Therefore, any condensate which accumulates in the lines will automatically, by gravity flow, drain into trap 15. With the liquid-pervious, gas-impervious membrane just over nozzle 35, condensate can then drain through the drain opening and the nozzle, while at the same time gases in the line are prvented from exiting through the drain opening. In this fashion, this patient breathing circuit remains pressurized during delivery of the gases, vapors or the like to the patient. Moreover, draining of condensate through the drain opening occurs continuously without the need to interrupt service to the patient to manually drain the trap as is necessary in the known water traps for patient breathing circuits. Once collection container 36 is filled, it can easily be emptied or replaced by the attendant with a new container without any interruption of the operation of the breathing apparatus.

Thus, the present invention provides a continuously draining trap for removal of condensate from a patient breathing circuit. No interruption of service to the patient is required when using this trap which allows the patient breathing circuit to operate under pressure even while the condensate is draining from the lines.

What is claimed is:

1. A trap for the continuous draining of condensate from an operational, pressurized breathing circuit adapted to deliver gases, vapors or the like to a patient comprising:
   a hollow, plastic Y-shaped tubular member having tubular lateraly extending side arms connected at one end thereof to a first end of a tubular base;
   a fluid inlet opening at the opposite end of one of said side arms of said Y-shaped member adapted for connection to a patient breathing apparatus and to receive pressurized fluid therefrom;
   a fluid outlet opening at the opposite end of the other of said side arms of said Y-shaped member adapted for connection to patient breathing means;
   a drain opening at the second end of the base of said Y-shaped member;
   a passageway inside said member providing fluid communication among all of the aforesaid openings; and
   a liquid-pervious, gas-impervious membrane covering said drain opening so that condensate in said member can continuously drain through said drain opening by force of gravity while the pressurized breathing circuit is passing fluid through said member up to pressures of about seven hundred (700) grams per square centimeter.

2. The trap of claim 1 wherein said membrane has a general pore size greater than 0.22 microns.

3. The trap of claim 1 wherein said membrane is made of cellulose with a general pore size of about 1.5 microns.

4. A patient breathing apparatus comprising:
   means for controllably providing fluid from a source under pressure to a patient in accordance with pre-established breathing rhythm;
   means for delivering said fluid under pressure to the patient; and
   means associated with said delivery means for allowing condensate, but not gas, in said delivery means to continuously and automatically drain therefrom while the fluid is being delivered to the patient under pressure, including a trap having: a hollow, plastic Y-shaped tubular member having tubular laterally extending side arms connected at one end thereof to a first end of a tubular base; a fluid inlet opening at the opposite end of one of said side arms of said Y-shaped member connected to said means for controllably providing fluid for receiving pressurized flud therefrom; a fluid outlet opening at the opposite end of the other of said side arms of said Y-shaped member connected to said means for delivering fluid to the patient; a drain opening at the opposite end of the base of said Y-shaped member; a passageway inside said member providing fluid communication among all of the aforesaid openings; and a liquid-pervious, gas-impervious membrane covering said drain opening so that condensate in said member can continuously drain through said drain opening by force of gravity while fluid is passing through the patient breathing apparatus up to pressures of about seven-hundred (700) grams per square centimeter.

5. A trap for the continuous draining condensate from an operational, pressurized breathing circuit adapted to deliver gases, vapors or the like to a patient comprising:
- a hollow, plastic three-port tubular member having tubular laterally extending side arms connected to one end thereof to a first end of a tubular base;
- a fluid inlet opening at the opposite end of one of said side arms of said three-port member adapted for connection to a patient breathing apparatus and to receive pressurized fluid therefrom;
- a fluid outlet opening at the opposite end of the other of said side arms of said three-port member adapted for connection to patient breathing means;
- a drain opening at the second end of the base of said three-port member;
- a passageway inside said member providing fluid communication among all of the aforesaid openings; and
- a liquid-pervious, gas-impervious membrane covering said drain opening so that condensate in said member can continuously drain through said drain opening by force of gravity while the pressurized breathing circuit is passing fluid through said member up to pressures of about seven hundred (700) grams per square centimeter.

* * * * *